United States Patent [19]

Skornia

[11] Patent Number: 5,611,812
[45] Date of Patent: Mar. 18, 1997

[54] PERFUSION CATHETER WITH BIFURCATED DISTAL END PORTION AND METHOD OF USING THE SAME

[75] Inventor: Edward Skornia, Pembroke Pines, Fla.

[73] Assignee: Cordis Corporation, Miami Lakes, Fla.

[21] Appl. No.: 570,649

[22] Filed: Dec. 11, 1995

[51] Int. Cl.$^6$ ................................................. A61M 25/10
[52] U.S. Cl. ................................................. 606/194; 604/96
[58] Field of Search ............................... 606/194; 604/96

[56] References Cited

U.S. PATENT DOCUMENTS

| | | |
|---|---|---|
| 4,655,746 | 4/1987 | Daniels et al. . |
| 4,909,252 | 3/1990 | Goldberger ............................... 606/194 |
| 4,983,167 | 1/1991 | Sahota ...................................... 606/194 |
| 5,002,531 | 3/1991 | Bonzel ................................... 606/194 X |
| 5,181,911 | 1/1993 | Shturman ............................. 606/194 X |
| 5,205,822 | 4/1993 | Johnson et al. . |
| 5,222,966 | 6/1993 | Perkins et al. . |
| 5,338,301 | 8/1994 | Diaz . |

*Primary Examiner*—Michael H. Thaler
*Attorney, Agent, or Firm*—Lockwood, Alex, Fitzgibbon & Cummings

[57] ABSTRACT

A bifurcated balloon catheter for use in dilation of blood vessels includes separate catheter shaft and distal end portions interconnected in a movable manner. The catheter shaft and distal end portion each include guidewire and inflation lumens extending therethrough which the moveable distal end portion includes a perfusion lumen which is exposed to blood flow when the catheter is rotated or twisted a blood vessel so that the distal end portion is displaced relative to the catheter shaft. A tube interconnects the catheter shaft and the distal end portion and provides an axis of rotation for the distal end portion.

20 Claims, 2 Drawing Sheets

PERFUSION CATHETER WITH BIFURCATED DISTAL END PORTION AND METHOD OF USING THE SAME

BACKGROUND AND SUMMARY OF THE INVENTION

The present invention relates generally to catheters used in angioplasty and perfusion procedures and more particularly, to a passive perfusion catheter which relies upon the blood flow within a vessel for perfusion.

Atherosclerosis is a condition characterized by fatty deposits accumulating on the interior walls of blood vessels. These deposits build up and harden and may build up to the point where they substantially block the flow of blood through the vessel. These blockages are referred to as stenoses. There are a variety of procedures and equipment used in the treatment of stenoses. The use of inflatable balloon, or dilation, catheters to treat such blockages is widespread. These balloon catheters are often used in percutaneous transluminal coronary angioplasty (PTCA) to treat such blockages by expanding against the blockage.

In PTCA, a guidewire is introduced into the artery of the patient and guided through the artery until the distal tip of the catheter is in the desired location of the blood vessel near the stenosis. A dilation catheter which has an inflatable balloon affixed to its distal end is then introduced along the guidewire and advanced into the patient until the balloon end, i.e., the distal end, is located at the stenosis. Once properly located, the balloon is inflated so that it expands against the artery walls, thereby expanding or dilating, the blood vessel and compressing the stenosis. This expansion often removes all of or a significant portion of the blockage. The balloon may be inflated against the arterial walls for one specific time or it may be repeatedly inflated and deflated in a cycle matching the heartbeat of the patient. Once the blood vessel is expanded, the balloon is deflated and the balloon and guidewire are removed so that blood may again flow through the blood vessel.

Restenosis is a condition where the blood vessel wall is expanded by the balloon and the blockage is opened, but the blood vessel wall contracts and adopts its original restricted state some time after the balloon is deflated and removed. The rate of restenosis may be lowered if longer inflation times are used during balloon catheterization procedures.

However, longer balloon inflation times may promote the occurrence of ischemia of the cardiac muscles and of the area surrounding the blood vessel. Ischemia is a local or temporary deficiency of oxygen in an area of the body caused by an obstruction in the blood vessel which supplies blood to that area. In order to prevent ischemia, perfusion catheters are used in association with balloon catheters and especially with coronary angioplasty catheters. Perfusion catheters are catheters which permit the continued flow of blood during the inflation of the balloon.

The perfusion of blood through a balloon at the distal end of a catheter may be accomplished in a number of ways. For example, an angioplasty balloon may be used which has one or more dedicated passages which define flow channels extending through the balloon from one end to the other to permit the passage of blood past the balloon and through the blood vessel. Alternatively, the balloon catheter itself may have a separate lumen dedicated as a fluid passage which extends through the catheter past the balloon, so that blood may be aspirated from another body location and pumped into the blood vessel past the blockage. In use, the balloon is inflated and deflated while blood is perfused through the balloon through a perfusion lumen. In such catheters, these pumps may be mechanically powered or may be hand-powered. In any event, when such pumps are used, they may create pressure pulses during operation. They may also affect the ability to perfuse blood through the vessel in vessels of small diameter.

The present invention is directed to a passive perfusion catheter which does not primarily rely upon an external pump and which has a bifurcated distal end portion having two separable, aligned components which may be displaced from alignment with each other to expose the openings of a perfusion lumen to the blood flowing within the blood vessel so that the flow of blood itself maintains perfusion through the distal end portion of the catheter.

Therefore, the present invention in one principal aspect includes a balloon catheter having a bifurcated distal end portion which includes two distinct components, one of the components supporting a dilation balloon and containing a perfusion lumen, the other of the two components containing a plurality of lumens, the one component being displaceable from an insertion position wherein the interior lumens of both components are axially aligned together along the length of the catheter to a perfusion position wherein a perfusion lumen is aligned within the blood vessel which permits the flow of blood through catheter.

In another principal aspect of the present invention, both catheter components include a guidewire lumen and an inflation lumen running therethrough which are aligned together when the catheter components are aligned in the insertion position. This position permits insertion and advancement of the catheter along a guidewire through the blood vessel to the site of the stenosis. The inflation lumen also extends through both catheter components when aligned in the insertion position and remains in alignment when the catheter is moved to a perfusion position wherein the component's perfusion lumen is aligned with the blood vessel and not with any lumen of the catheter.

In still another principal aspect of the present invention, the inflation lumen of the two catheter components serves to interconnect the components by means of a transit tube which permits displacement of one catheter component relative to the other catheter component. In a preferred embodiment of the invention this movement is rotational, so that when the catheter distal end portion is inserted into a blood vessel and positioned in place at the stenoses, a physician need only twist the proximal end of the catheter to displace the distal end portion of the catheter from the rest of the catheter.

It is therefore an object of the present invention to provide an improved perfusion catheter having a bifurcated distal end defining two components of the catheter which permits movement of one component relative to the other component.

Another object of the present invention is to provide a passive perfusion catheter which relies upon the flow within a blood vessel to accomplish the perfusion without the aid of an external pump.

Still another object of the present invention is to provide a perfusion catheter having a bifurcated distal end portion dividing the catheter into two components, each of the components having distinct guidewire and inflation lumen portions, these portions being axially aligned together when the catheter is in an insertion position, the two components being moveable out of alignment with each other by twisting or rotating the catheter so that the inflation lumen portions are aligned but the guidewire lumen portions are not aligned, the one catheter component containing a perfusion lumen which is exposed and defines a fluid passage within a blood vessel when displaced from the other catheter component.

Yet another object of the present invention is to provide a method for dilating a blockage within a blood vessel while possibly perfusing blood past the blockage by inserting a catheter of the aforementioned construction into a blood vessel, locating the distal end portion of the catheter carrying an inflation balloon, manipulating the catheter to displace the distal end portion out of alignment with the rest of the catheter thereby exposing the perfusion lumen thereof, and inflating the balloon while permitting blood to perfuse past the balloon.

These and other objects, features and advantages of this invention will be clearly understood through a consideration of the following detailed description.

BRIEF DESCRIPTION OF THE DRAWINGS

In the course of the following detailed description, reference will be frequently made to the accompanying drawings in which.

DETAILED DESCRIPTION OF THE PREFERRED EMBODIMENTS

Figure 1:
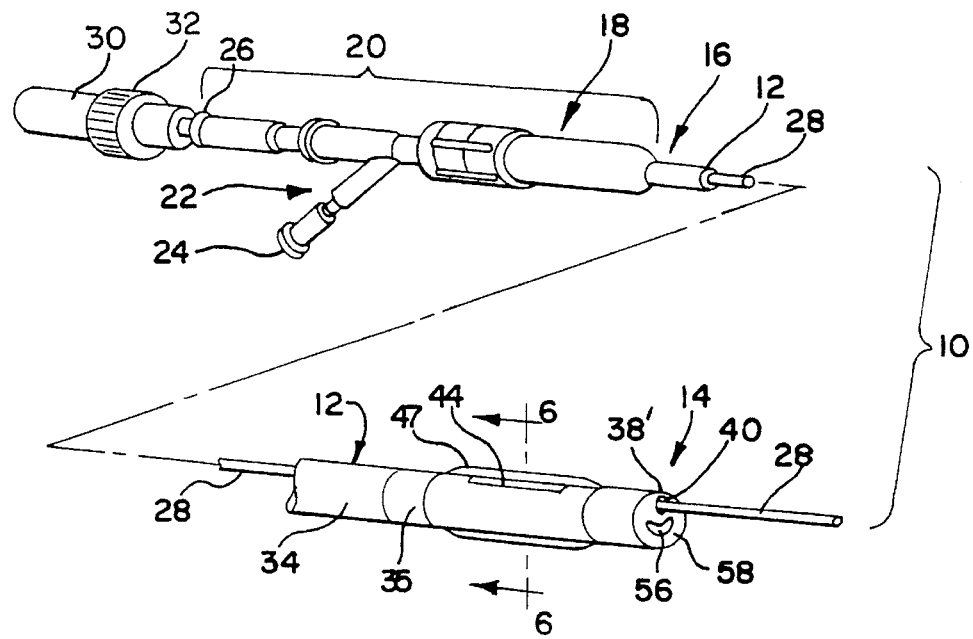
FIG. 1 is an exploded perspective view of a catheter constructed in accordance with the principles of the present invention with certain portions of the catheter removed.

Turning first to FIG. 1, a dilation catheter constructed in accordance with the principles of the present invention is generally illustrated at 10. The catheter 10 includes an elongated catheter body 12 having a distal end 14 and a proximal end 16. The proximal end 16, as is known in the art, is preferably connected to a connector 18 in the form of a manifold 20. Portions of the manifold 20 may include an inflation port 22 having an adapter 24 which is adapted to receive the operative end of an injection device (not shown) by which a suitable dilation or inflation fluid, such as a saline solution, may be injected to dilate the catheter dilation balloon 47.

Aft of the inflation port 22, a guidewire port 26 is located which receives a manipulatable guidewire 28 therein and a guidewire manipulator 30 illustrated as a knurled knob 32. The guidewire 28, as is known in the art, extends through the manifold 20 and through the catheter 10 for substantially its entire length. Preferably, the guidewire 28 has a length which is somewhat greater than the length of the catheter 10 so that a portion of the distal end 29 of the guidewire 28 projects past the distal end 14 of the catheter 10 when the catheter 10 is advanced into position within the blood vessel 50.

In an important aspect of the present invention, the catheter body 12 is bifurcated. That is, the catheter body 12 includes two interconnected components 34, 35 which are displaceable relative to each other. These components include an elongated catheter shaft portion 34 and a displaceable catheter distal end portion 35. These two components are interconnected by a suitable means 36 as will be explained in greater detail below. Both catheter components 34, 35 may be suitably formed by way of an extrusion process from compatible materials such as organic polymers and typically a thermoplastic such as nylon, polyurethane, polyethyleneterepthalate (PET), polyvinlychloride (PVC), polyethylene and the like. The catheter components 34, 35 may be formed in either an unreinforced manner or in reinforced with suitable metal wires, braided metal cable or the like. The catheter body may typically have a length of from between 60 cm to 150 cm and an outer diameter which ranges between French sizes 3 to 11, with a French size being equal to about 0.33 mm, the range being about 1 mm to 3.7 mm. For use in coronary applications, the catheter body 11 may typically have a length of turn about 120 cm to about 150 cm and diameters of about 3 to 11 French.

The catheter body 11, and particularly the catheter body shaft portion 34, includes at least a pair of passages or lumens 38, 39 which extend for the entire length of the shaft portion 34. One such lumen 38 receives and houses the guidewire 28 for the entire length of the catheter 10 and terminates at an opening 40 at the distal end 14 of the catheter 10. This distal end 14 includes a distal endface 42 of the catheter distal end portion 35. The guidewire lumen 38 extends rearwardly to the proximal end 16 of the catheter 10 where it meets with an appropriate passage (not shown) extending from the guidewire port 30. The guidewire lumen 38 is separated into two portions 38 and 38' which are respectively disposed in the catheter shaft and distal end portions 34, 35 of the catheter body 12.

Figure 2:
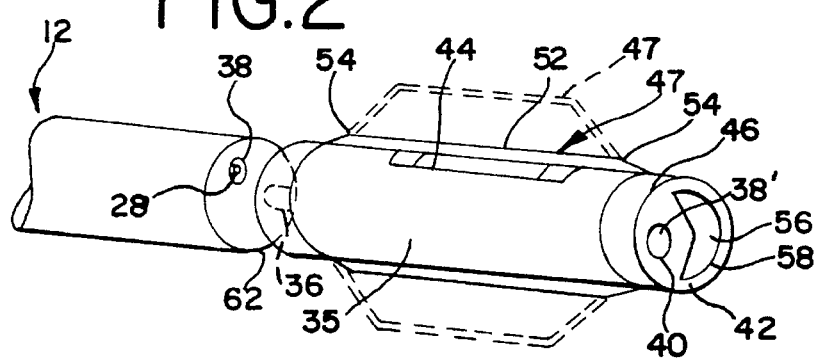
FIG. 2 is an enlarged perspective view of the distal end portion of the catheter of FIG. 1 illustrating the catheter in a perfusion position wherein the catheter distal end portion is displaced from the catheter shaft portion and out of axial alignment therewith.
Figure 3:
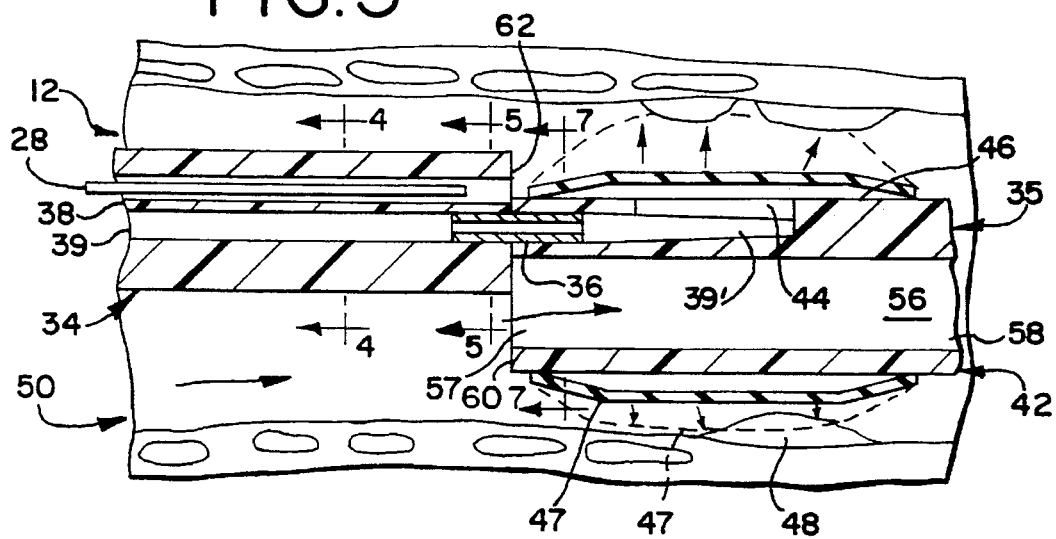
FIG. 3 is a partial longitudinal cross-sectional elevational view of the distal end portion of the catheter of FIGS. 1 & 2 inserted into a blood vessel.
Figure 4:
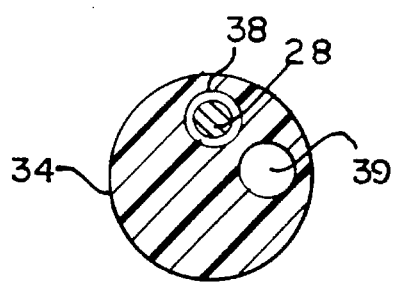
FIG. 4 is a cross-sectional view of the catheter shaft portion of the catheter of FIG. 3 taken generally along lines 4—4 thereof.
Figure 5:
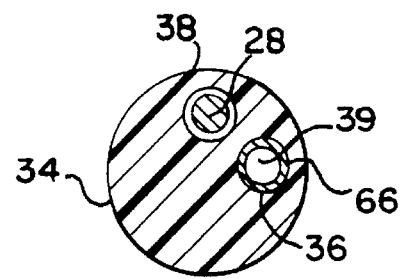
FIG. 5 is a cross-sectional view of the catheter shaft portion of the catheter of FIG. 3 taken near its distal end generally along lines 5—5 thereof.
Figure 6:
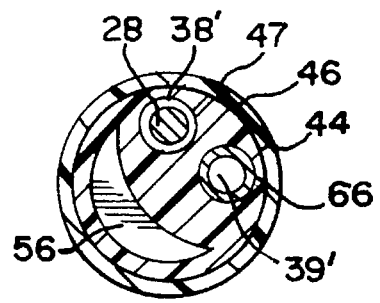
FIG. 6 is a cross-sectional view of the catheter distal end portion of the catheter of FIG. 1 taken generally along lines 6—6 thereof.
Figure 7:
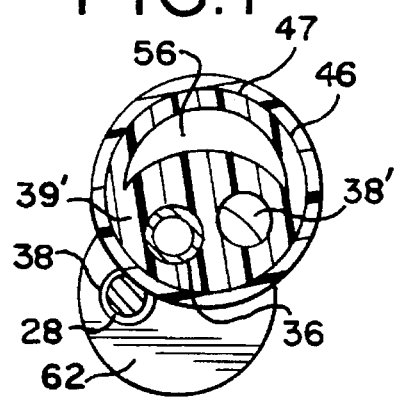
FIG. 7 is a cross-sectional view of the catheter distal end portion of the catheter of FIG. 3 taken generally along lines 7—7 thereof.

The other catheter lumen 39 serves as an inflation or perfusion lumen and also extends through the catheter shaft portion 34 as well as part of the catheter distal end portion 35 by way of respective lumen portions 39, 39' (FIGS. 2 and 3). The perfusion lumen terminates near the distal end 14 of the catheter 10 in an opening 44 which communicates with the exterior surface 46 of the catheter distal end portion 35. The lumen 39 extends rearwardly to the catheter proximal end 16 where it meets with an opening of the inflation port 22. This lumen 39 defines a fluid passage, or conduit, which conveys a dilation fluid through the lumen 39, 39' and out of the opening 44 where it dilates the balloon 47 against a blockage 48 in a blood vessel 50. The dilation balloon 46 preferably has a hollow, elongated balloon body portion 52 of a preselected length with two opposing neck portions 54 which tightly engage the exterior surface 46 of the distal end portion 35 of the catheter 10 to provide a fluid tight seal therebetween.

In another important aspect of the invention, the catheter distal end portion 35 preferably includes a separate perfusion lumen 56 extending lengthwise therethrough to define a fluid passage between two opposite openings 57, 58 formed in the opposing endfaces 42, 60 of the distal end portion 35. As will be explained in detail below, when the distal end portion 35 is aligned axially with the catheter shaft portion 34, the perfusion lumen is unexposed to blood flow in the blood vessel 50, indicated by the arrows in FIG. 3, and when the distal end portion 35 is displaced into a perfusion portion as illustrated in FIG. 3, the perfusion lumen 56 is exposed and blood may flow through under its own pressure to thereby accomplish passive perfusion of blood through the blood vessel 50 and past the blockage 48.

In the insertion position, the catheter shaft and distal end portions 34, 35 are axially aligned so that the guidewire and inflation lumens 38, 38' and 39, 39' thereof are aligned axially. In this manner, the guidewire 28 may be inserted into the blood vessel 50 and manipulated into place along the guidewire 28 at or near the blockage 48 so that the catheter body 12 may be subsequently advanced along the guidewire 28 until the distal end 14 thereof reaches the site of the blockage 48. When in place at the blockage, the user partially withdraws the guidewire 28 a sufficient amount so that the guidewire 28 leaves its lumen portion 38' in the catheter distal end portion 35 (at least past the endface 62 as shown in FIGS. 2 & 3).

Figure 9:
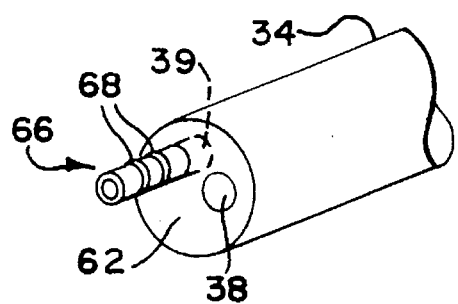

The two catheter body components 34, 35 are interconnected by a suitable means 36, illustrated in the figures as a hollow hypo tube 66 which is interfitted in the inflation lumen 39 at the junction of the two body components 34, 35, i.e. across the interface defined by their two opposing endfaces 60, 62. This tube 66 is preferably a metal tube and may, as illustrated in FIG. 9, include irregularities 68 on its outer surface 70 to engage the interior walls of the inflation lumen 39, 39' to resist axial movement therebetween yet permit rotation of either the tube 66 within the lumen 39 or the lumen 39 around the tube 66. The engagement between the tube and the inflation lumen portions 39 is preferably fluid tight to prevent leakages under injection pressure of the inflation media, which typically occur at about 3 atmospheres or more. The interfitting of the tube 66 in the inflation lumen portions 39 preferably also permits the catheter distal end portion 35 to be displaced out of alignment with the catheter shaft portion 34 by manipulating the catheter 10 to apply a rotational or twisting force to catheter body shaft distal end portions 34, 35 after the guidewire 28 is removed from the distal end portion. Such a force will cause rotation one of the two catheter components 34, 35 with respect to the other around an axis of rotation centered about the tube 66.

Figure 8:
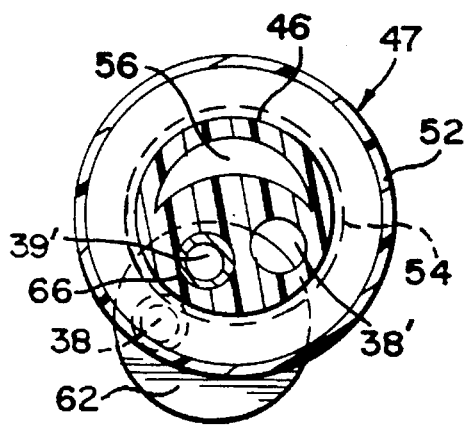
FIG. 8 is a cross-sectional view of the catheter of FIGS. 1 & 2 taken through the distal end portion thereof illustrating the displacement of the distal end portion and inflation of the dilation balloon thereof; and, FIG. 9 is a perspective view of an interconnecting element used to interconnect the two catheter components together in place within the catheter body but with the head portion removed for clarity.

The present invention may be used effectively in balloon dilation procedures without the need for an external perfusion pumping apparatus. In such procedures, as explained above, the catheter shaft distal end portions 34, 35 are aligned together and inserted onto the guidewire 28 so that the catheter may traverse the same path as the guidewire 28. When located at the blockage site, the guidewire 28 may be partially withdrawn in its lumen 28 and the catheter body 12 twisted to displace the distal end portion 35 out of phase, or alignment into the position illustrated in FIG. 3. An inflation media is thereupon injected through the perfusion lumen 39 which passes through the opening 44 of the distal end portion 35 and causes the balloon 47 to inflate (FIG. 8).

While the balloon 47 is dilated, the perfusion lumen 56 presents a channel or passage through the blockage 48 for blood to flow passively, under its own pressure. The balloon 47 may be repeatedly inflated and deflated to compress the blockage.

While the preferred embodiment of the invention have been shown and described, it will be understood by those skilled in the art the changes or modifications may be made thereto without departing from the true spirit and scope of the invention.

I claim:

1. A balloon dilation catheter for active dilation and passive perfusion within a blood vessel having proximal and distal ends, the catheter comprising: a flexible, catheter shaft carrying an inflatable dilation balloon adjacent the distal end, said catheter having a guidewire lumen and an inflation lumen extending at least most of the length of said catheter, said catheter further having a perfusion lumen, said catheter shaft having two distinct portions, one of said portions being a catheter shaft body portion and the other of said portion being a catheter shaft head portion, said perfusion lumen extending through said catheter shaft head portion, said catheter shaft body and head portions lying adjacent each other along a longitudinal axis of said catheter, said guidewire and inflation lumens extending substantially through both of said catheter shaft body and head portions, said catheter shaft body and head portions being displaceable relative to each other such that said catheter shaft head portion may be displaced from said catheter shaft body portion after insertion of said catheter into said blood vessel from an initial insertion position wherein said catheter shaft body and head portions are aligned with each other along said catheter longitudinal axis such that said guidewire lumen extends in alignment through said catheter shaft body and head portions to a subsequent working position wherein said catheter shaft body and head portions are not aligned along said catheter longitudinal axis to expose said perfusion lumen to flow of blood within said blood vessel and such that said guidewire lumen opens at the distal end of said catheter shaft body portion rather than at the distal end of said catheter shaft head portion, said inflation lumen extending from said catheter shaft body portion to said catheter shaft head portion.

2. The catheter as defined in claim 1, further including means interconnecting opposing surfaces of said catheter shaft body and head portions, said means permitting said relative movement between said catheter shaft body and head portions.

3. The catheter as defined in claim 2, wherein said catheter shaft body and head portion interconnecting means includes a hollow tube extending between said catheter shaft body and head portions opposing surfaces.

4. The catheter as defined in claim 3, wherein said hollow tube is disposed in said inflation lumen and further interconnects portions of said inflation lumen disposed in said catheter body and head portions to provide a continuous fluid passage therebetween.

5. The catheter as defined in claim 3, wherein said hollow tube includes at least one engagement surface which engages said catheter shaft body and head portions in a manner which resists axial movement therebetween but permits rotational movement therebetween.

6. The catheter as defined in claim 1, wherein said perfusion lumen extends between opposing ends of said catheter shaft head portion, said perfusion lumen further having two distinct openings disposed opposite each other at said catheter shaft head portion ends such that an open fluid passage is defined in said catheter shaft head portions when said catheter shaft body and head portions are moved out of axial alignment with each other.

7. The catheter as defined in claim 1, wherein said catheter proximal end includes a hub connecting to said guidewire lumen which permits the mounting of guidewire manipulation means on said catheter proximal end.

8. The catheter as defined in claim 1, wherein said catheter shaft head portion includes an opening disposed thereon communicating with said inflation lumen for conveying an expansion media to said balloon.

9. The catheter as defined in claim 1, wherein said balloon includes an elongated body portion extending between two opposing neck portions, the balloon neck portions having a general diameter less than a general diameter of said balloon body portion and less than a general diameter of said catheter shaft, whereby said balloon neck portions engage an exterior surface of said catheter shaft in a fluid-tight manner.

10. The catheter as defined in claim 9, wherein said balloon is disposed entirely upon said catheter shaft head portion and said balloon neck portions engage an exterior surface of said catheter shaft head portion.

11. The catheter as defined in claim 1, further including means for aligning said catheter shaft body and head portions together.

12. The catheter as defined in claim 11, wherein said catheter shaft body and head portion alignment means includes means for preventing relative movement of said catheter shaft head and body portions in one preselected direction but permitting said relative movement in another direction.

13. A catheter for use in dilating a blood vessel and having a bifurcated distal end portion, comprising:

an elongated catheter for insertion into a blood vessel, the catheter having a proximal end and a distal end and multiple lumens disposed within said catheter, a first of said lumens including a guidewire lumen, a second of said lumens including an inflation lumen and a third of said lumens including a perfusion lumen, said catheter including a bifurcated body, the bifurcated body including a catheter shaft portion and a distal end portion aligned together along a longitudinal axis of said catheter, said catheter distal end portion extending rearwardly from said catheter distal end until it abuts said catheter shaft portion, the catheter distal end portion being moveable about a predesignated axis of rotation with respect to said catheter shaft portion when said catheter shaft portion is subjected to a preselected rotational force after insertion of said catheter into said blood vessel, said guidewire and inflation lumens each having two distinct portions respectively extending axially through said catheter shaft and distal end portions, said perfusion lumen being disposed solely in said catheter distal end portion and defining a fluid passage extending therethrough having fluid openings at opposite ends of said catheter distal end portion, whereby when said catheter is inserted into said blood vessel and subjected to said preselected rotational force, said catheter distal end portion moves away from said catheter shaft portion by rotating said catheter shaft portion with said preselected rotational force about said axis of rotation to expose said perfusion lumen to blood flow within said body vessel; and a dilation balloon disposed on said catheter distal end portion, an opening of said inflation lumen disposed on said catheter distal end portion, the catheter distal end portion including means joining said catheter distal end portion to said catheter shaft portion.

14. The catheter as defined in claim 13, wherein said catheter shaft and distal end portion joining means includes a hollow tube extending between said catheter shaft and said catheter distal end portion and providing a continuous passage for said inflation lumen throughout the length of said catheter.

15. The catheter as defined in claim 14, wherein said hollow tube is aligned with said axis of rotation.

16. The catheter as defined in claim 13, wherein said catheter distal end portion is moveable about said axis of rotation between first and second operative positions, wherein in said first operative position said catheter distal end portion of said guidewire lumen portion is aligned with said guidewire lumen portion of said catheter shaft, whereby a guidewire may be inserted said catheter proximal end through the entire length of said catheter and exit a guidewire opening in said catheter distal end and wherein in said catheter second operative position, said catheter tip guidewire lumen portion is not aligned with said remainder of said catheter guidewire lumen, whereby a guidewire exits only through an opening of said guidewire lumen of said catheter shaft.

17. The catheter as defined in claim 14, wherein said hollow tube has engagement means disposed thereon which prevents axial movement between said catheter shaft and distal end portion yet permits rotational movement therebetween.

18. A method of perfusing a blood vessel while dilating a blockage within a blood vessel, comprising the steps of:

providing a dilation balloon catheter having a catheter shaft portion and a distal end portion which is displaceable from the shaft portion upon manipulation, the catheter having a guidewire lumen and a balloon dilation lumen extending for substantially the length of said catheter, the guidewire and balloon dilation lumens each having respective distinct shaft and distal end portions respectively fixedly disposed in said catheter shaft and distal end portions, said balloon dilation distal end portion terminating in a dilation opening on an exterior surface of said distal end portion, said distal end portion also having a perfusion lumen extending therein to provide a fluid passage therethrough, said distal end portion further including a dilation balloon disposed on an exterior surface thereof and encompassing said balloon dilation lumen opening;

inserting said catheter into a blood vessel of a patient and transiting the blood vessel until said distal end portion is in the vicinity of said blockage;

manipulating said catheter to apply a force to said catheter shaft in order to displace said distal end portion from said catheter shaft portion to thereby displace said distal end portion into a perfusion position within said blood vessel so that said perfusion lumen is in fluid communication with said blood vessel; and, dilating said balloon against said blockage by injecting a dilation fluid through said balloon dilation lumen.

19. The method of claim 17, when said step of manipulating said catheter includes rotating said catheter shaft.

20. The method of claim 17, wherein said step of manipulating said catheter includes twisting said catheter shaft.

* * * * *